United States Patent
Turner et al.

(10) Patent No.: US 9,139,505 B2
(45) Date of Patent: Sep. 22, 2015

(54) PRODUCTION OF TEREPHTHALIC ACID DI-ESTERS USING ALCOHOL-AMINE PROMOTERS

(71) Applicant: Eastman Chemical Company, Kingsport, TN (US)

(72) Inventors: Phillip Wayne Turner, Blountville, TN (US); Steven Leroy Cook, Kingsport, TN (US); Anthony Gerard Barrett, Rio de Janeiro (BR)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/075,606

(22) Filed: Nov. 8, 2013

(65) Prior Publication Data

US 2015/0133683 A1    May 14, 2015

(51) Int. Cl.
  C07C 51/265    (2006.01)
  C07C 67/08     (2006.01)

(52) U.S. Cl.
  CPC .............. *C07C 67/08* (2013.01); *C07C 51/265* (2013.01)

(58) Field of Classification Search
  CPC .................................................... C07C 51/265
  USPC ................................ 560/99; 562/412, 416
  See application file for complete search history.

(56) References Cited

U.S. PATENT DOCUMENTS

| | | |
|---|---|---|
| 2,569,440 A | 10/1951 | Agnew et al. |
| 3,886,199 A | 5/1975 | Suter et al. |
| 3,896,159 A | 7/1975 | Kratzer et al. |
| 4,150,214 A | 4/1979 | Kelley |
| 4,216,337 A | 8/1980 | Baba et al. |
| 4,241,216 A | 12/1980 | Bergman et al. |
| 4,619,987 A | 10/1986 | Saiki et al. |
| 4,681,975 A | 7/1987 | Hasegawa et al. |
| 4,952,663 A | 8/1990 | Cleary et al. |
| 5,102,979 A | 4/1992 | Miki et al. |
| 5,296,587 A | 3/1994 | Sumner, Jr. et al. |
| 5,349,075 A | 9/1994 | van den Berg et al. |
| 5,428,126 A | 6/1995 | Kashima et al. |
| 5,502,240 A | 3/1996 | Pugach et al. |
| 5,741,882 A | 4/1998 | Fujii et al. |
| 5,886,133 A | 3/1999 | Hilbert et al. |

(Continued)

FOREIGN PATENT DOCUMENTS

| | | |
|---|---|---|
| JP | 55-164220 | 12/1980 |
| JP | 60-004151 | 1/1985 |

(Continued)

OTHER PUBLICATIONS

Y. Mansoori et al., "Esterification of carboxylic acids by tributyl borate under solvent- and catalyst-free conditions," Green Chem., vol. 7, pp. 870-873 (2005).

(Continued)

*Primary Examiner* — Kamal Saeed
*Assistant Examiner* — Janet L Coppins
(74) *Attorney, Agent, or Firm* — Phan Law Group PLLC

(57) ABSTRACT

The invention is directed to a process for preparing a terephthalic acid di-ester. The process includes contacting terephthalic acid with a $C_6$-$C_{10}$ alcohol in the presence of an organotitanium catalyst and an alcohol-amine promoter under conditions effective to form a corresponding terephthalic acid di-ester. The promoter can improve the reaction time by as much as 50%.

20 Claims, 1 Drawing Sheet

(56) References Cited

U.S. PATENT DOCUMENTS

| | | |
|---|---|---|
| 5,922,828 A | 7/1999 | Schiraldi |
| 6,303,738 B1 | 10/2001 | Putzig et al. |
| 6,310,233 B1 | 10/2001 | Maurer et al. |
| 6,559,271 B2 | 5/2003 | Schaaf et al. |
| 6,664,413 B1 | 12/2003 | Cockrem |
| 6,916,950 B2 | 7/2005 | Gubisch et al. |
| 6,982,295 B2 | 1/2006 | Godwin et al. |
| 7,271,282 B1 | 9/2007 | Kawahara et al. |
| 7,276,621 B2 | 10/2007 | Cook et al. |
| 7,323,586 B2 | 1/2008 | Wiese et al. |
| 7,326,764 B2 | 2/2008 | Di et al. |
| 7,368,522 B2 | 5/2008 | Jernigan et al. |
| 7,696,300 B2 | 4/2010 | Ohta et al. |
| 7,799,942 B2 | 9/2010 | Osborne et al. |
| 7,842,361 B2 | 11/2010 | Ohta et al. |
| 8,034,970 B2 | 10/2011 | Hassan et al. |
| 8,207,289 B2 | 6/2012 | Jernigan |
| 8,263,728 B2 | 9/2012 | Kono et al. |
| 2006/0160986 A1 | 7/2006 | Hazen |
| 2007/0038001 A1 | 2/2007 | Cook et al. |
| 2012/0202928 A1 | 8/2012 | Loos et al. |

FOREIGN PATENT DOCUMENTS

| | | | |
|---|---|---|---|
| JP | 63-317523 | 12/1988 | |
| KR | 20130008344 A | 1/2013 | |
| WO | 95/29888 A1 | 11/1995 | |
| WO | WO 2008/140177 | * 11/2008 | ............. C08L 31/08 |

OTHER PUBLICATIONS

P. Jiang, "Synthesis of DOTP Plasticizer by Esterification," Huaxue Shijie, vol. 35, pp. 411-415 (1994) (Abstract Only).
Y.K. Yang et al., "New Titanium-Based Catalysts for the Synthesis of Poly(Ethylene Terephthalate)," Bull. Korean Chem. Soc., vol. 33, pp. 3445-3447 (2012).
International Search Report and Written Opinion issued in Int'l Application No. PCT/US2014/063880, pp. 1-12 (Jan. 30, 2015).
English Abstract of KR 2013-0008344 A (2013).
English Machine Translation of KR 2013-0008344 A (2013).
English Abstract of JP 55-164220 (1980).
English Abstract of JP 60-004151 (1985).
English Abstract of JP 63-317523 (1988).

* cited by examiner

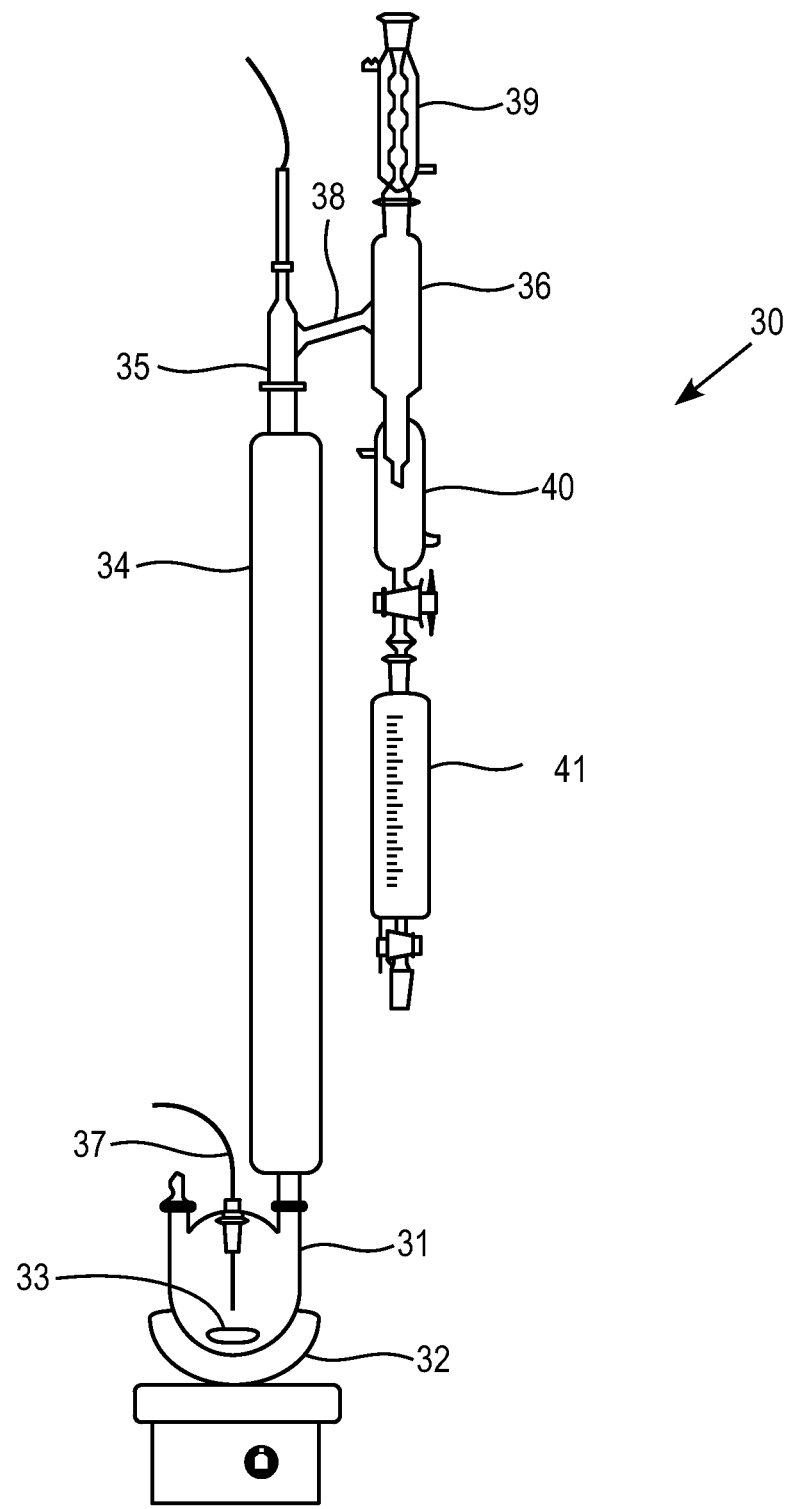

PRODUCTION OF TEREPHTHALIC ACID DI-ESTERS USING ALCOHOL-AMINE PROMOTERS

FIELD OF THE INVENTION

The invention generally relates to the preparation of terephthalic acid di-esters from terephthalic acid.

BACKGROUND OF THE INVENTION

Terephthalic acid di-esters, such as di-(2-ethylhexyl) terephthalate (also known as dioctyl terephthalate or DOTP), can be used as plasticizers in a variety of polymeric materials such as polyvinyl chloride.

DOTP is typically prepared by the titanate-catalyzed transesterification of dimethyl terephthalate (DMT) with 2-ethylhexanol (EH). This method, however, is not the most direct route to making DOTP. It requires the conversion of terephthalic acid (TPA) to DMT.

The most direct route to DOTP involves esterification of TPA with EH. Organo-titanates, such as tetraisopropoxy titanate, are among the best catalysts for this direct route. The reaction rate with these catalysts, however, is still significantly slower than the transesterification route.

Therefore, there is a need in the art for faster methods for forming DOTP directly from TPA.

The present invention addresses this need as well as others, which will become apparent from the following description and the appended claims.

SUMMARY OF THE INVENTION

The invention is as set forth in the appended claims.

Briefly, the present invention provides a process for preparing a terephthalic acid di-ester. The process comprises contacting terephthalic acid with a $C_6$-$C_{10}$ alcohol in the presence of an organo-titanium catalyst and an alcohol-amine promoter under conditions effective to form a corresponding terephthalic acid di-ester. The promoter is selected from 2-(methylamino)ethanol and 2-(ethylamino)ethanol.

In one embodiment, the invention provides a process for preparing di-(2-ethylhexyl) terephthalate. The process comprises contacting terephthalic acid with 2-ethylhexanol in the presence of an organo-titanium catalyst and an alcohol-amine promoter at a temperature of 140 to 230° C. to form di-(2-ethylhexyl) terephthalate. The promoter is selected from 2-(methylamino)ethanol and 2-(ethylamino)ethanol. The contacting step is carried out in a reactor fitted with a fractionation column comprising three to six high-efficiency theoretical stages for removing water from the reactor.

BRIEF DESCRIPTION OF THE DRAWING

The FIGURE shows a reactor and column useful with the process according to the present invention.

DETAILED DESCRIPTION OF THE INVENTION

It has been surprisingly discovered that certain alcohol-amines can significantly improve the reaction rate of organo-titanium catalyzed esterification of terephthalic acid with a $C_6$-$C_{10}$ alcohol to make the corresponding di-ester.

The present invention provides a process for preparing a terephthalic acid di-ester. The process comprises contacting terephthalic acid with a $C_6$-$C_{10}$ alcohol in the presence of an organo-titanium catalyst and an alcohol-amine promoter under conditions effective to form a corresponding terephthalic acid di-ester.

Examples of $C_6$-$C_{10}$ alcohols include hexanol, cyclohexanol, heptanol, 2-ethylhexanol (EH or 2-EH), cyclohexanemethanol, isomers of methylcyclohexanemethanol, octanol, nonanol, benzyl alcohol, 2-phenyl ethanol, and decanol.

Examples of the type of terephthalic acid di-esters that can be produced include dihexyl terephthalate, diheptyl terephthalate, di-(2-ethylhexyl) terephthalate, dibenzyl terephthalate, dinonyl terephthalate, and didecyl terephthalate.

Examples of suitable organo-titanium catalysts include titanium tetraalkoxides having the formula $Ti(OR)_4$ where R is an alkyl group having 1 to 8 carbon atoms. A preferred organo-titanium catalyst includes tetraisopropoxy titanate. The catalyst may be used in amounts ranging from 1000 to 2000 ppm, 1200 ppm to 1600 ppm, and 1300 ppm to 1500 ppm, based on the total reactant charge.

The preferred alcohol-amine promoters include 2-(methylamino)ethanol and 2-(ethylamino)ethanol. 2-(Ethylamino) ethanol is particularly preferred. The promoter may be used in amounts ranging from 500 ppm to 1500 ppm, 750 ppm to 1250 ppm, and 1100 ppm to 1200 ppm, based on the total reactant charge.

The process according to the invention may be carried out in a batch or continuous reactor under esterification conditions. The reactor can be a simple, stirred unit fitted with a fractionation column for water removal or can contain multiple ports for reactant introduction and product removal.

In one embodiment, the reactor is fitted with a fractionation column and access ports for charging TPA, alcohol, promoter, and catalyst. The fractionating column can both increase the reaction rate and minimize the occurrence of foaming as described in U.S. Pat. No. 7,799,942 (the entire content of which is hereby incorporated by reference).

In another embodiment, the fractionation column has three to six high-efficiency theoretical stages (HETS). To minimize foaming, the fractionation column can have four to five HETS.

Typical esterification conditions include atmospheric pressure and elevated temperature. The temperature for reaction is typically set based on the lowest boiling point of the reactants, which is usually the alcohol. Generally, the temperature for reaction can range, for example, from 140 to 230° C., or from 180 to 225° C.

The esterification can be carried out with an excess amount of the alcohol. The mole ratio of alcohol to acid employed can range from 3:1 to 6:1, or 5:1 to facilitate conversion to the diester. Unreacted alcohol can be readily recycled to the process.

The process according to the invention may be practiced in a continuous mode by adding the TPA to a suitable reactor by means of a screw feeder and the alcohol/catalyst as a pump-fed mixture to a stirred-reactor equipped with a fractionating column/decanter combination such that the water of reaction can be removed and the unreacted alcohol returned to the reactor. The effluent from this reactor can be passed to a chain of one or more finishing reactors where the conversion to di-ester and removal of water are continued. The product of this reaction can be further processed and refined as described herein, if desired.

In one particular embodiment, the reactor is charged with terephthalic acid, excess 2-ethylhexanol, and a catalytic amount of tetraisopropoxy titanate (which is commonly abbreviated as TIPT), and the organic rate promoter. Heating and stirring the mixture to reflux results in efficient removal of water and esterification of the TPA to DOTP. The volatile components are mainly composed of the water of reaction and the unreacted 2-ethylhexanol. The water can be separated via a decanter, and the 2-ethylhexanol is allowed to reflux throughout the column. Conversion to DOTP is essentially complete in less than two hours, and the product can be filtered to remove traces of unreacted TPA for recycle. The crude product (filtrate) is then neutralized with dilute NaOH, washed with water, and filtered. Excess 2-ethylhexanol is stripped off at reduced pressure. An activated carbon treatment can be used to reduce color in the final product.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations. These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90 and 70 to 80.

This invention can be further illustrated by the following examples of preferred embodiments thereof, although it will be understood that these examples are included merely for purposes of illustration and are not intended to limit the scope of the invention.

EXAMPLES

Example 1

Esterification of TPA with 2-EH Using Various Promoter Candidates

This example used the reactor system and associated distillation column 30 shown in the FIGURE. The equipment included a one-liter base 31 fitted with a heating mantel 32, a magnetic stirrer bar 33, a temperature sensor 37, and a distillation column 34. The column 34 contained 10 inches of Penn State packing (which is equivalent to approximately 5 HETS). The top of the column 34 was fitted with a head 35 to allow the water/2-ethylhexanol azeotrope to condense via a condenser 39 and collect in a decanter 36. The top 2-ethylhexanol layer in the decanter 36 was returned to the column 34 via an overflow tube 38, and the water layer was collected in a collection device 40 and cooled in cooler 41 for weighing.

The reactor column base 31 was charged with 343.48 g (2.637 moles, 25 mole % excess, MW=130.23) of 2-ethylhexanol, 1.054 mole (175 g, MW=166.13) of purified terephthalic acid (PTA), 3000 ppm of promoter candidate (1.55 g) listed in Table 1, and 3000 ppm (1.55 g) of tetraisopropoxy titanate (TIPT). In the case of promoter candidate DEA Titanate, 6000 ppm was used since it is thought to be a roughly 1:1 complex of organo-titanium and diethanol amine.

The decanter was charged with 36.6 g of 2-ethylhexanol to make up for the removal of the 25 mole % excess from the system.

Heat-up was started, and the reaction progress was monitored by the production of water. The total water removed was typically 40-42 g. A 98.5% recovery of materials was typically achieved. Table 1 shows the promoter candidates tested and the total reaction time to achieve completion for each candidate.

TABLE 1

| Run | Promoter | Structure | Reaction Time (hrs.) |
|---|---|---|---|
| 1 | 2-(ethylamino)ethanol | HO~~~N(H)~~~ | 2.50 |
| 2 | 2-(methylamino)ethanol | HO~~~N(H)~ | 2.75 |
| 3 | 2-(butylamino)ethanol | HO~~~N(H)~~~~ | 3.25 |
| 4 | 2-aminoethanol | HO~~~NH$_2$ | 3.25 |
| 5 | N-methyl diethanol amine | HO~~~N(~)~~~OH | 4.25 |
| 6 | 2-(benzylamino)ethanol | HO~~~N(H)~Ph | 3.50 |
| 7 | Triethylamine | N(Et)$_3$ | 3.50 |
| 8 | Diethylamine | ~~N(H)~~ | 3.25 |
| 9 | Pyridine | pyridine ring | 3.50 |
| 10 | DEA Titanate (6000 ppm) | Proprietary | 3.00 |
| 11 | Diethanol Amine | HO~~~N(H)~~~OH | 3.50 |
| 12 | 1H-pyrrole | pyrrole ring | 3.50 |

Example 2

A designed experiment was conducted to determine the optimum levels of reactants (TPA and EH), promoter (EAE), and catalyst (TIPT) for the conversion of TPA to DOTP. The parameters of the experiment are shown in Table 2.

TABLE 2

| 2-ethylhexanol (EH) | EH/TPA Mole Ratio |
|---|---|
| High | 5 |
| Middle | 4 |
| Low | 3 |

TABLE 2-continued

| 2-(ethylamino)ethanol (EAE) | Promoter Conc. (ppm) |
|---|---|
| High | 1500 |
| Middle | 1000 |
| Low | 500 |

| tetraisopropoxy titanate (TIPT) | Catalyst Conc. (ppm) |
|---|---|
| High | 1500 |
| Middle | 1000 |
| Low | 500 |

0.5 moles of TPA were used.

The reaction was conducted as described in Example 1 above. The overall reaction time (defined as accumulation of the theoretical water of reaction) was the sole response. The run number was chosen randomly. The results of the designed experiment are summarized in Table 3 below.

TABLE 3

| Run Number | EH | EAE | TIPT | Reaction Time (hrs) |
|---|---|---|---|---|
| 7 | H | H | H | 1.70 |
| 17 | H | H | M | 2.80 |
| 16 | H | H | L | 4.00 |
| 6 | H | M | H | 1.60 |
| 9 | H | M | M | 1.90 |
| 20 | H | M | L | 3.30 |
| 15 | H | L | H | 2.70 |
| 12 | H | L | M | 2.00 |
| 23 | H | L | L | 3.90 |
| 18 | M | H | H | 1.70 |
| 3 | M | H | M | 2.50 |
| 24 | M | H | L | 4.25 |
| 22 | M | M | H | 1.90 |
| 5 | M | M | M | 2.50 |
| 10 | M | M | L | 3.75 |
| 27 | M | L | H | 2.10 |
| 21 | M | L | M | 2.25 |
| 13 | M | L | L | 3.70 |
| 2 | L | H | H | 2.25 |
| 26 | L | H | M | 2.50 |
| 1 | L | H | L | 4.00 |
| 25 | L | M | H | 2.25 |
| 14 | L | M | M | 2.40 |
| 19 | L | M | L | 4.00 |
| 8 | L | L | H | 2.40 |
| 4 | L | L | M | 2.50 |
| 11 | L | L | L | 3.90 |
| Centerpoint 1 | M | M | M | 2.25 |
| Centerpoint 2 | M | M | M | 2.50* |
| Centerpoint 3 | M | M | M | 2.20 |
| Centerpoint 4 | M | M | M | 2.40 |

The "*" next to the reaction time for Centerpoint 2 in Table 3 indicates the reproducibility of a particular experiment and is used by statisticians to establish the standard deviation for "identical conditions."

The "*" next to the reaction time for Centerpoint 2 in Table 3 indicates the reproducibility of a particular experiment and is used by statisticians to establish the standard deviation for "identical conditions."

The results in Table 3 were analyzed and a statistical model developed. The model indicated that the optimum level of 2-EH was 2.5:0.5 (5:1 mole ratio), the optimum level of promoter EAE was 1144 ppm, and the optimum TIPT amount was 1412 ppm. This set of calculated conditions would result in a reaction time of about 1.75 hours, which is within the experimental error of the values listed in Table 3.

Example 3 (Comparative)

Example 2 was compared with an optimized dimethyl terephthalate run using the same reaction equipment. The following were charged to the flask: 364.6 g of 2-ethylhexanol (2.8 moles, 40 mole % excess, MW=130.23); 194.2 g of DMT (1 mole; MW=194.18); and 0.055 g of TIPT (98 ppm).

A total of 1.4 hours reaction time resulted in removing 255 mL of methanol to completion of the reaction. Thus, the best reaction time achievable with terephthalic acid of 1.75 hours compares favorably with the 1.4 hours reaction time obtained with dimethyl terephthalate.

Example 4 (Comparative)

This example was conducted using the same reaction conditions and equipment as Run 12 of Example 2, but at twice the scale and with no promoter.

The reactor column base was charged with 651.2 g (5 moles, 150 mole % excess, MW=130.23) of 2-ethylhexanol, 1.00 mole (166.1 g, MW=166.13) of purified terephthalic acid, and 1000 ppm (0.818 g) of tetraisopropoxy titanate. The decanter was charged with 36.6 g of 2-ethylhexanol to make up for the removal of the 25 mole % excess from the system. Heat-up was started, and the reaction progress was monitored by the production of water. The total water removed was 36.2 g. The total reaction time to complete reaction was 3.75 hours.

Run 12 of Example 2 (with EAE as promoter) gave a reaction time of 2.0 hours. The promoter reduced the total reaction time by 47%.

The invention has been described in detail with particular reference to preferred embodiments thereof, but it will be understood that variations and modifications can be effected within the spirit and scope of the invention.

We claim:

1. A process for preparing a terephthalic acid di-ester, comprising:
    contacting terephthalic acid with a $C_6$-$C_{10}$ alcohol in the presence of an organo-titanium catalyst and an alcohol-amine promoter under conditions effective to form a corresponding terephthalic acid di-ester,
    wherein the promoter is selected from 2-(methylamino)ethanol and 2-(ethylamino)ethanol.

2. The process according to claim 1,
    wherein the $C_6$-$C_{10}$ alcohol is selected from hexanol, heptanol, 2-ethylhexanol, octanol, nonanol, and decanol, and
    wherein the corresponding terephthalic acid di-ester is selected from di-(hexyl) terephthalate, di-(heptyl) terephthalate, di-(2-ethylhexyl) terephthalate, di-(octyl) terephthalate, di-(nonyl) terephthalate, and di-(decyl) terephthalate.

3. The process according to claim 1, wherein the $C_6$-$C_{10}$ alcohol is 2-ethylhexanol and the corresponding terephthalic acid di-ester is di-(2-ethylhexyl) terephthalate.

4. The process according to claim 1, wherein the organo-titanium catalyst is a titanium tetraalkoxide having the formula $Ti(OR)_4$ where R is an alkyl group having 1 to 8 carbon atoms.

5. The process according to claim 1, wherein the organo-titanium catalyst is tetraisopropoxy titanate.

6. The process according to claim 1, wherein the conditions effective to form a corresponding terephthalic acid di-ester comprise a temperature of 180 to 225° C.

7. The process according to claim 1, which comprises carrying out the contacting step in a reactor fitted with a fractionation column for removing water from the reactor.

8. The process according to claim 7, wherein the fractionation column comprises three to six high-efficiency theoretical stages.

9. The process according to claim 1, wherein the promoter comprises 2-(ethylamino)ethanol.

10. The process according to claim 1, wherein the contacting step is carried out at a $C_6$-$C_{10}$ alcohol to terephthalic acid molar ratio of 3:1 to 6:1.

11. The process according to claim 1, wherein the alcohol-amine promoter is present in an amount of 500 to 1,500 ppm based on the total amount of terephthalic acid and $C_6$-$C_{10}$ alcohol.

12. The process according to claim 1, wherein the organo-titanium catalyst is present in an amount of 1,000 to 2,000 ppm based on the total amount of terephthalic acid and $C_6$-$C_{10}$ alcohol.

13. A process for preparing di-(2-ethylhexyl) terephthalate, comprising:
   contacting terephthalic acid with 2-ethylhexanol in the presence of an organo-titanium catalyst and an alcohol-amine promoter at a temperature of 140 to 230° C. to form di-(2-ethylhexyl) terephthalate,
   wherein the promoter is selected from 2-(methylamino)ethanol and 2-(ethylamino)ethanol, and
   wherein the contacting step is carried out in a reactor fitted with a fractionation column comprising three to six high-efficiency theoretical stages for removing water from the reactor.

14. The process according to claim 13, wherein the organo-titanium catalyst is a titanium tetraalkoxide having the formula $Ti(OR)_4$ where R is an alkyl group having 1 to 8 carbon atoms.

15. The process according to claim 13, wherein the organo-titanium catalyst is tetraisopropoxy titanate.

16. The process according to claim 13, wherein the contacting step is carried out at a temperature of 180 to 225° C.

17. The process according to claim 13, wherein the promoter comprises 2-(ethylamino)ethanol.

18. The process according to claim 13, wherein the contacting step is carried out at a 2-ethylhexanol to terephthalic acid molar ratio of 3:1 to 6:1.

19. The process according to claim 13, wherein the alcohol-amine promoter is present in an amount of 500 to 1,500 ppm based on the total amount of terephthalic acid and 2-ethylhexanol.

20. The process according to claim 13, wherein the organo-titanium catalyst is present in an amount of 1,000 to 2,000 ppm based on the total amount of terephthalic acid and 2-ethylhexanol.

\* \* \* \* \*